United States Patent
Strauch

(10) Patent No.: US 11,156,591 B2
(45) Date of Patent: Oct. 26, 2021

(54) METHOD FOR CALIBRATING A GAS CHROMATOGRAPH

(71) Applicant: Siemens Aktiengesellschaft, Munich (DE)

(72) Inventor: Piotr Strauch, Ruelzheim (DE)

(73) Assignee: Siemens Aktiengesellschaft, Munich (DE)

(*) Notice: Subject to any disclaimer, the term of this patent is extended or adjusted under 35 U.S.C. 154(b) by 333 days.

(21) Appl. No.: 16/320,852

(22) PCT Filed: Jul. 26, 2017

(86) PCT No.: PCT/EP2017/068921
§ 371 (c)(1),
(2) Date: Jan. 25, 2019

(87) PCT Pub. No.: WO2018/019903
PCT Pub. Date: Feb. 1, 2018

(65) Prior Publication Data
US 2019/0162707 A1 May 30, 2019

(30) Foreign Application Priority Data
Jul. 27, 2016 (EP) .................................... 16181353

(51) Int. Cl.
*G01N 30/86* (2006.01)
*G01N 33/00* (2006.01)
(Continued)

(52) U.S. Cl.
CPC ......... *G01N 30/8665* (2013.01); *G01N 30/04* (2013.01); *G01N 30/8651* (2013.01);
(Continued)

(58) Field of Classification Search
CPC ........... G01N 30/8665; G01N 30/8672; G01N 33/0006; G01N 33/0008; G01N 33/007;
(Continued)

(56) References Cited

U.S. PATENT DOCUMENTS 5,710,713 A * 1/1998 Wright ................. G01N 21/274
250/282
2003/0066803 A1 4/2003 Wright
(Continued)

FOREIGN PATENT DOCUMENTS

CN 103675182 3/2014
CN 105051529 11/2015
(Continued)

OTHER PUBLICATIONS

Karen Rome, Allyson McIntyre: "Intelligent use of relative response factors in gas chromatography-flame ionisation detection", Chromatography Today, pp. 52-56, XP002763884, the whole document; May 1, 2012.
(Continued)

*Primary Examiner* — Herbert K Roberts
(74) *Attorney, Agent, or Firm* — Cozen O'Connor

(57) ABSTRACT

Method for calibrating a gas chromatograph to render the calibration of the gas chromatograph more error-proof, wherein relative response factors determined during the calibration are compared with universal relative response factors contained in the memory and typical of the detectors, where an error message is generated and output if the relative response factors determined in the calibration deviate beyond a predetermined degree from the universal relative response factors, and where the universal relative response factors are determined and provided for different components by the manufacturer of the detectors, for instance.

17 Claims, 2 Drawing Sheets

(51) Int. Cl.
*G01N 30/04* (2006.01)
*G01N 30/88* (2006.01)
*G01N 30/62* (2006.01)
*G01N 35/00* (2006.01)
*G01N 30/02* (2006.01)

(52) U.S. Cl.
CPC ......... *G01N 30/8658* (2013.01); *G01N 30/88* (2013.01); *G01N 33/0006* (2013.01); *G01N 33/0008* (2013.01); *G01N 33/0063* (2013.01); *G01N 2030/025* (2013.01); *G01N 2030/625* (2013.01); *G01N 2035/009* (2013.01)

(58) Field of Classification Search
CPC ....... G01N 35/00693; G01N 35/00702; G01N 2030/626
See application file for complete search history.

(56) References Cited

U.S. PATENT DOCUMENTS

| | | | |
|---|---|---|---|
| 2006/0265141 A1 | 11/2006 | Wang et al. | |
| 2012/0016597 A1* | 1/2012 | Sutan | G01N 30/8665 702/24 |
| 2013/0304393 A1* | 11/2013 | Sutan | G01N 30/8665 702/22 |
| 2014/0051092 A1 | 2/2014 | Williams et al. | |
| 2014/0260509 A1* | 9/2014 | Pohl | G01N 30/02 73/1.02 |

FOREIGN PATENT DOCUMENTS

| | | |
|---|---|---|
| WO | WO03/083467 | 10/2003 |
| WO | WO 2006/121878 A3 | 12/2007 |
| WO | WO 2012/140429 A2 | 10/2012 |

OTHER PUBLICATIONS

Guidelines for the quantitative gas chromatography of volatile flavouring substances, from the Working Group on Methods of Analysis of the International Organization of the Flavor Industry (IOFI), Flavour and Fragrance Journal, 2011, 26, 297-299.
Office Action dated Jun. 29, 2020 issued in Chinese Patent Application No. 201780046398.4.
Li Guogang, "Guidelines for Quality Management of Environmental Monitoring," China Environment Science Press, Aug. 31, 2010, pp. 33-37.
Lin, G., "Microprocessor and Instrument Control", Yunyang Publishing House, Jun. 30, 1980, pp. 239-240.
Office Action dated Feb. 24, 2021 issued in Chinese Patent Application No. 201780046398.4.
ISA, "Calibration," "ISA-RP 12.13—Part II—1987, Installation, Operation and Maintenance of Combustible Gas Detection Instruments," p. 16, Jul. 31, 1987.
United Nations Economic and Social Council, "Tbtal VOCs Concentration measurement techniques etc.,"—"Executive Body for the Convention on Long-range Transboundary Air Pollution, Fifty-Third Session," pp. 1-2, 8, 9, 24-25, Dec. 17, 2015.
Office Action dated Aug. 20, 2021 issued in Chinese Patent Application No. 201780046398.4.
Lin, Zaikang et al. "Mining CAD Design Software and Applications", China University of Mining and Technology Press, 2008, (3 pages).

* cited by examiner

METHOD FOR CALIBRATING A GAS CHROMATOGRAPH

CROSS-REFERENCE TO RELATED APPLICATIONS

This is a U.S. national stage of application No. PCT/EP2017/068921 filed Jul. 26, 2017. Priority is claimed on EP Application No. 16181353 filed Jul. 27, 2016, the content of which is incorporated herein by reference in its entirety.

BACKGROUND OF THE INVENTION

1. Field of the Invention

The invention relates to a method for calibrating a gas chromatograph and to a gas chromatograph.

2. Description of the Related Art

As known, for instance, from WO 03/083467 A2, with the gas chromatographic analysis of a mixture of materials, a dosed sample of the (gaseous or if necessary evaporated) mixture of materials is routed through a chromatographic separating device with the aid of a carrier gas. Here, the components of the mixture of materials are separated due to different retention times, so that they appear one after the other at the output of the separating device. The individually emerging components are detected there via a suitable detector. To this end, different types of detectors, such as heat conduce detectors or flame ionization detectors, are available. The heat conductivity detector used in most instances compares the heat conductivity of the currently detected component with that of the carrier gas and in the process generates a detector response in the form of a (ideally gaseous) peak, the surface of which is normally proportional to the volume of the detected component. For the duration of the analysis of the mixture of materials, the detector therefore generates a chromatogram, in which the local or temporal positions of the peaks refer to the different components and the peak surfaces (or on more simple inspection the peak heights) the volumes of the components in the sample of the mixture of materials given to the gas chromatograph. By evaluating the chromatogram, the concentrations of the different components are determined in the mixture of materials.

While a separating column as a separating device is adequate for separating simple mixtures of materials, complex mixtures of materials require a column switching, in which two or more separating columns with different separation properties are switched consecutively in series and possibly in parallel. In this case, detectors (generally heat conductivity detectors) can be arranged downstream of the individual separating columns and detect the eluting components in a nondestructive manner and together form a detector device.

The detector response, in particular the peak surface used to quantitatively determine the detected component, is primarily dependent on the component, its volume and the detector used in each case. Moreover, the detector response is influenced by the different measuring conditions, such as temperature, pressure and flow rate of the carrier gas, operating voltage of the detector, or amplification of the detector raw signal.

It is therefore necessary to calibrate the gas chromatograph for the different components to be determined of the gas mixture to be analyzed.

The calibration can be performed individually for each component to be determined, by a calibration sample which contains the respective component in a known concentration $c_i$ being given to the gas chromatograph. An absolute response factor $RF_i = A_{i,cal}/c_{i,cal}$ can be determined therewith, where $c_{i,cal}$ refers to the concentration of the component i in the calibration sample and $A_{i,cal}$ refers to the resulting detector response in the form of the peak surface. Provided that with the analysis of a gas mixture containing the component i in an unknown concentration, the same measuring conditions exist as with the calibration (where in particular the dosed sample volume is also the same) and the detector behaves linearly across the concentration measurement range, the concentration $c_i$ of the component i can be determined from the detector response $A_i$ with $c_i = A_i/RF_i$ by using the determined absolute response factor $RF_i$. With non-linear behavior of the detector, the calibration must be performed with a number of calibration samples with different known concentration values of the component, in order to produce a calibration curve for the detector.

It is very difficult to accurately reproducibly dose the same sample quantity every time. As such, it is known to add an internal standard IS in a specific concentration $c_{IS}$ to the calibration sample and the samples of gas mixtures to be analyzed in each case. Since with the calibration the response factors $RF_i$ and $RF_{IS} = A_{IS}/c_{IS}$ have been determined for the component i and the standard IS, during the analysis the concentration $c_i$ of the component i can be determined from the detector response $A_i$ with $c_i = c_{IS} \cdot (A_i \cdot RF_{IS})/(RF_i \cdot A_{IS})$. The unknown concentration $c_i$ is therefore measured in relation to the known concentration $c_{IS}$, where the relation is independent of the respectively dosed sample quantity.

The response factor $RF_i$ of the component i can be set in relation to the response factor $RF_{IS}$ of the standard IS, so that a relative response factor $RRF_{i\text{-}IS} = RF_i/RF_{IS}$ is obtained, on the basis of which the concentration $c_i$ of the component i can be determined with $c_i = c_{IS} \cdot (1/RRF_{i\text{-}IS}) \cdot (A_i/A_{IS})$.

Relative response factors can generally be used to determine an unknown concentration $c_i$ of a first component i of a mixture of materials in the presence of a second component (reference component) k, the concentration $c_k$ of which is known. It is therewith possible to also measure the concentrations $c_i$ of components i for which there is no separate response factor $RF_i$ or the following has been determined via calibration: $c_i = c_k \cdot (1/RRF_{i\text{-}k}) \cdot (A_i/A_k) = A_i/(RF_k \cdot RRF_{i\text{-}k})$.

The relative response factors $RRF_{i\text{-}k}$ must also be determined within the scope of a calibration. The advantage of its use is that in a valid scope of application they are independent of the dosed sample quantity (dosage) and the measuring conditions; new components can be added to the calibration mixture, and it is possible to convert the relative response factors into other reference components; in other words e.g.: $RRF_{j\text{-}k} = RRF_{j\text{-}i} \cdot RRF_{i\text{-}k}$. With an unknown relative response factor $RRF_{j\text{-}k}$ but known relative response factors $RRF_{j\text{-}i}$ and $RRF_{i\text{-}k}$, the concentration $c_j$ of a component j can therefore be determined as follows: $c_j = c_k \cdot (1/(RRF_{j\text{-}i} \cdot RRF_{i\text{-}k})) \cdot (A_j/A_k) = A_j/(RF_k \cdot RRF_{j\text{-}i} \cdot RRF_{i\text{-}k})$.

Response factors can also be defined and calculated otherwise, for instance, as a reciprocal value of the aforementioned factors. Reference is made to the following citations with respect to the prior art:

"Guidelines for the quantitative gas chromatography of volatile flavouring substances, from the Working Group on Methods of Analysis of the International Organization of the Flavor Industry (IOFI)", Flavour and Fragrance Journal, 2011, 26, 297-299.

K. Rome et al.: "Intelligent use of Relative Response Factors in Gas Chromatography-Flame Ionisation Detection", Chromatography Today, May/June 2012, 52-56.

Calibration methods for chromatographs are also known from US 2014/260509 A1 or US 2003/066803 A1.

US 2014/260509 A1 discloses a liquid chromatograph into which a standard solution with at least two analytes is injected in differently known concentrations for calibration purposes, so that peaks with different peak heights or surfaces and different retention times are obtained as a detector response. The two analytes are independent of the sequence in which they emerge from the chromatographic separating device and thus independent of the separating device used or its state identifies its peak heights or surfaces on the basis of the relationship. With a recalibration, the retention times obtained for the two analytes are monitored to determine whether they have changed by more than one predetermined degree, compared with the first calibration. If this is the case, then a message is generated stating that the separating device has to be replaced.

US 2003/066803 A1 describes a method for calibrating a light-scattering detector (Evaporative Light Scattering Detector (ELSD)), which is used in conjunction with a liquid chromatograph. A solvent with chromatographically separated components of a mixture of materials dissolved therein is nebulized and evaporated in the detector. The solid particles of the components that are produced in the process are routed through a light beam and the light scattered at the particles is detected. The detector response is a peak with a surface proportional to the mass of the detected component and is moreover dependent on the composition of the solvent. In order to calibrate the detector, a solvent with solid particles dissolved therein is injected into these samples, where the organic composition of the solvent, the solid substances and the solid mass are varied. The calibration data including the determined peak surfaces is stored. With the chromatographic analysis of a mixture of materials, the obtained peak surfaces and the known composition of the solvent used is compared with the calibration data, in order to immediately determine the masses of the sought components of the mixture of materials from the calibration data or via interpolation.

Errors during the calibration of a chromatograph in general or gas chromatographs in particular can considerably affect the accuracy of the chromatographic analysis. Therefore, due to errors on the part of the user, such as due to a mistake, incorrect calibration mixtures can be used, or e.g. with input errors incorrect information relating to the calibration mixture can be transferred into the evaluation device of the gas chromatograph. The calibration mixture itself may have been changed due to leakages in the gas bottle, dirt, aging, so that it no longer corresponds to the specification. The parameterization of the gas chromatograph may have also been changed. Further error sources are, e.g., leakages and inadequate rinsing of the gas paths through the gas chromatograph.

SUMMARY OF THE INVENTION

In view of the foregoing, it is therefore an object of the invention to make the calibration of a gas chromatograph more error-proof.

This and other objects and advantages are achieved in accordance with the invention by a gas chromatograph and a method for calibrating the gas chromatograph which comprises a dosing device, a separating device, a detector device and an evaluation device, which are arranged and configured to dose a sample of a mixture of materials to be analyzed, route the dosed sample to separate components contained in the mixture of materials via the separating device, detect selected separated components at the end thereof and to quantitatively determine their concentrations in the mixture of materials based on detector responses supplied by the detector device and response factors stored in the evaluation device, where the determination of the concentration of at least one first component of the mixture of materials is performed as a function of the detector response to this component, the determined or known concentration of a second component of the mixture of materials and a relative response factor.

In accordance with the invention, with the calibration one or more samples of one or more calibration mixtures, which contain the components in known concentrations, is analyzed in the gas chromatographs and the relative response factors are determined based on the obtained detector responses and the known concentrations and are stored in the evaluation device.

Moreover, with the calibration, the determined relative response factors in the evaluation device are compared with universal relative response factors typical of the detector device, and an error message is generated and output by the evaluation device, if the relative response factors determined during the calibration deviate beyond a predetermined degree from the universal relative response factors.

The term "response factor" or "relative response factor" is not only to be understood in the narrow sense of an individual factor but can, instead, particularly with non-linear behavior of the detector, also represent a "response function" or "relative response function" across the concentration measurement area.

The knowledge underlying the invention is that the detectors currently used in gas chromatography have very high reproducibility on account of series production. This applies in particular to microtechnically produced (MEMS) detectors, such as heat conductivity detectors. Owing to this high reproducibility, the relative response factors of the detectors are practically unchangeable and have a universal character. The universal relative response factors can therefore, e.g., with the manufacturer of the gas chromatographs and/or detectors, be determined for different components and given to the detectors in the form of a device description, for instance, or can be called up electronically, such as on a remote computer (cloud) that can be accessed via the internet. The device description with the universal relative response factors can be stored on a data carrier, which can be read out in a wired and/or wireless manner by the evaluation device of the gas chromatograph. For instance, the data carrier can be formed as a storage chip, e.g., in the form of an RFID tag, on the detector device or the detectors forming the same.

In the event that deviations extending beyond the predetermined degree are established for a number of components, the evaluation device can identify a deviation pattern and on the basis of this report an error cause. This can take place by comparison with predetermined deviation patterns, to which different errors are assigned.

The invention allows a user to signal possible errors during the calibration and also to output notifications of error causes to him.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

To further explain the invention, reference is made below to the figures, in which.

DETAILED DESCRIPTION OF THE EXEMPLARY EMBODIMENTS

Figure 1:
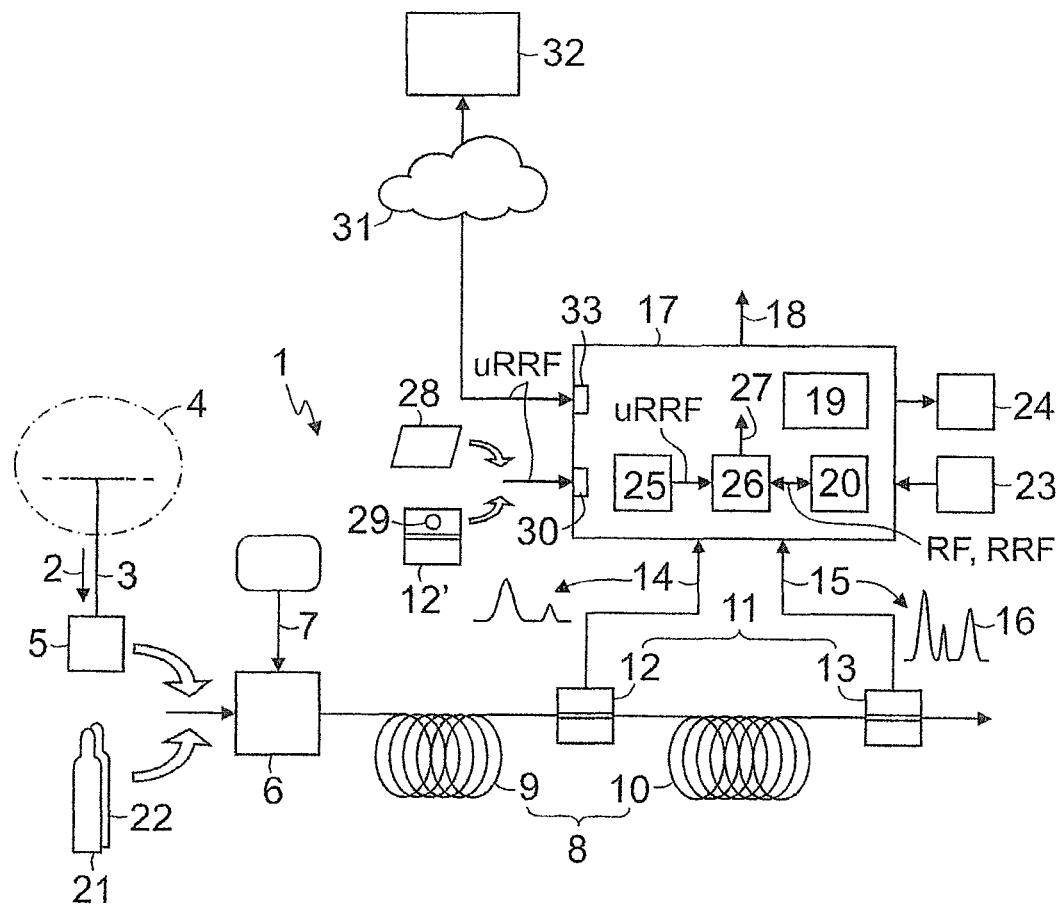
FIG. 1 shows an exemplary gas chromatograph in accordance with the invention.

With reference to FIG. 1, the very simplified gas chromatograph 1 shown is used to analyze a mixture of materials 2, which is taken from a technical process 4 by way of a line 3. The mixture of materials 2 is possibly prepared, such as evaporated, in a preparation device 5 for the chromatographic analysis, before it is given to the gas chromatograph 1. In a dosing device 6, a sample in the form of the shortest possible and sharply limited dosing plug is ejected from the mixture of materials 2 and is then routed via a carrier gas 7 through a separating device 8. The separating device 8 can, in a known manner, consist of an individual separating column, or, as shown here, of a circuit of two or more separating columns 9, 10. When passing through the separating device 8, the components of the mixture of materials 2 contained in the dosed sample are separated, so that they emerge temporally one after the other from the separating device 8 and are detected via a detector device 11. In the illustrated example, the detector device 11 has two detectors 12, 13, where the detector 12 detects a predetermined number of components emerging from the separating coil 9 and until then sufficiently separated, and the detector 13 detects the remaining components after their separation in the separating coil 10. If possible, the components detected by the detector 12 can be ejected from the separating device 8 before reaching the separating column 10.

The detectors 12, 13 each supply a chromatogram in which a detector response in the form of a peak, e.g., 16, appears for each detected component, as a detector signal 14 or 15, the height and surface area of which depends on a detection-specific property of the component, its volume in the sample and the detector used. In the exemplary illustrated embodiment, the detectors 12, 13 are microtechnically produced (MEMS) heat conductivity detectors, so that the detection-specific property of the component is its heat conductivity compared with that of the carrier gas 7. The chromatograms 14, 15 are evaluated in an evaluation device 17 arranged downstream of the detector device 8, in order to quantitatively determine selected components of the mixture of materials 2 to be analyzed and finally to output the same as an analysis result 18. Here, the concentration of each component in a computing unit 19 is calculated as a function of the respective detector response (peak) 16 to this component and a response factor is calculated, which has been determined within the scope of a calibration for the relevant component and has been stored in a calibration data memory 20.

As already mentioned at the start, the response factors generally describe the reaction of the detector to different components, in other words in an individual case the association between the concentration of a specific detected component and the detector response resulting therefrom. This association can be an individual value or a function dependent on the concentration. Typically, absolute response factors RF specify the relationship between the detector response and the concentration. Relative response factors RRF are used to describe the reaction of the detector to a specific component with respect to the reaction of the detector to another specific component. Typically, a relative response factor RRF specifies the relationship between two response factors RF for different components. If the detector behaves the same with both components, then the relative response factor RRF is equal to one. Relative response factors RRF can be formed from absolute and/or relative response factors RF, RRF.

The response factors RF, RRF are determined within the scope of a calibration, where samples of calibration mixtures 21, 22 that contain components or mixtures of the components of interest with predetermined concentrations are given to the gas chromatograph 1. The evaluation device 17 calculates the response factors RF, RRF and stores these in the calibration data memory 20 from the detector responses (peaks) 16 generated during the analysis of the calibration samples for the different components and the associated known concentration values that are input into the evaluation device 17 by the user. To this end, means for inputting 23 the known concentration values and visualizing 24 the detector responses prepared by the evaluation device 17 (e.g. keyboard and display, touchscreen, external PC) are available to the user. The determination and storage of the response factors RF, RRF is supported and monitored by the user as required or is performed automatically. Insofar as this is performed via an external PC or suchlike, for instance, within the meaning of the invention this can be considered to be an integral part of the evaluation device 17. The evaluation device (electronic part) 17 can also be arranged spatially separated from the analysis part of the gas chromatograph 1.

The evaluation device 17 has a further memory 25, in which universal relative response factors uRRF are stored, which have been determined once for the used detectors or detector types 12, 13 and different components. The relative response factors RRF determined during the calibration are compared in a comparison device 26 of the evaluation device 17 with the universal relative response factors uRRF, where an error message 27 is generated as soon as relative response factors RRF determined during the calibration deviate by a predetermined degree from the associated universal relative response factors uRRF. As already explained further above, relative response factors for specific components can be converted into other reference components. Consequently, the comparison also comprises those relative response factors RFF and/or universal relative response factors uRRF not immediately determined by measurement but instead computationally. The error message 27 and preferably also the sum of the deviation are communicated to the user, e.g., indicated on the visualization means 24. In this way, possible errors in the calibration are signaled to the user and notifications as to the error causes are possibly output. If an excessive deviation occurs between the determined relative response factors RRF and the associated universal relative response factors uRRF with all components of a calibration mixture, e.g. 22, for instance, this can indicate an error in the calibration mixture 22. If deviations result with a number of or all calibration mixtures 21, 22, an error may exist in the gas chromatograph 1 or its operation. Singular deviations with individual components indicate a possible input error on the part of the user. Based on a further deviation pattern, the evaluation device 17 can identify a mistake in the calibration mixture used as a possible error and communicate the same to the user, for instance.

The detectors 12, 13 used in the gas chromatograph 1, in particular the heat conductivity detectors produced microtechnically and used here by way of example, have a very high reproducibility on account of series production. Owing to this high reproducibility, the relative response factors RRF of the detectors 12, 13 are practically unchangeable and have a universal character. The universal relative response factors uRRF can therefore be determined by the manufacturer for different components, for instance, and given to the detectors in the form of a device description, for instance. With the exemplary illustrated embodiment, this is performed for instance via a separate data carrier 28, such as a USB stick or a data carrier, such as memory chip 29, on the detector 12', into which the universal relative response factors uRRF are written. This information can be read out in a wired or wireless manner via a suitable data interface 30 of the evaluation device 17 and transmitted into the memory 25. In addition or alternatively, the universal relative response factors uRRF can be provided on a remote computer 32 (cloud) which can be accessed via the internet 31.

Figure 2:
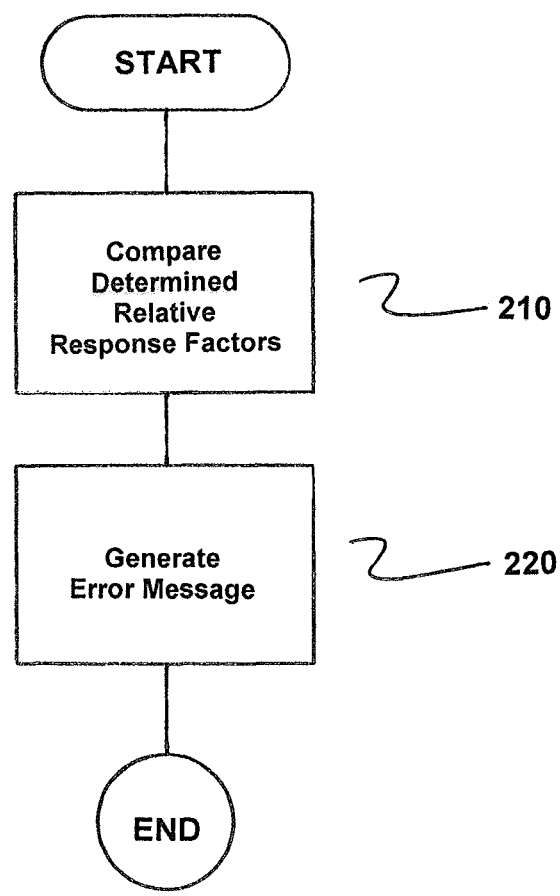
FIG. 2 is a flowchart of the method in accordance with the invention.

FIG. 2 is a flowchart of the method for calibrating a gas chromatograph 1 which comprises a dosing device 6, a separating device 8, a detector device 11 and an evaluation device 17, which are arranged and configured to dose a sample of a mixture of materials 2 to be analyzed, route the dosed sample in order to separate components contained in the mixture of materials 2 via the separating device 8, detect selected separated components at the end thereof and to quantitatively determine their concentrations in the mixture of materials 2 based on detector responses 6 supplied by the detector device 11 and response factors RF, RRF stored in the evaluation device 17, where a determination of the concentration of at least one first component of the mixture of materials 2 is performed as a function of a detector response 16 to the at least one first component, a determined or known concentration of a second component of the mixture of materials 2 and a relative response factor RRF, and where at least one sample of at least one calibration mixture 21, 22, which contains components in known concentrations, is analyzed in the gas-chromatograph 1 based on the calibration and relative response factors RRF are determined based on the obtained detector responses 16 and the known concentrations and are stored in the evaluation device 17.

The method comprises comparing, based on the calibration, the determined relative response factors RRF in the evaluation device 17 with universal relative response factors uRRF typical of the detector device 11, as indicated in step 210.

Next, an error message 27 by the evaluation device 17 is generated and output, if the relative response factors RRF determined during the calibration deviate beyond a predetermined degree from the universal relative response factors uRRF, as indicated in step 220.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for calibrating a gas chromatograph, which comprises a dosing device, a separating device, a detector device and an evaluation device, which are arranged and configured to dose a sample of a mixture of materials to be analyzed, route the dosed sample in order to separate components contained in the mixture of materials via the separating device, detect selected separated components at the end thereof and to quantitatively determine their concentrations in the mixture of materials based on detector responses supplied by the detector device and response factors stored in the evaluation device, a determination of a concentration of at least one first component of the mixture of materials being performed as a function of a detector response to the at least one first component, a determined or known concentration of a second component of the mixture of materials and a relative response factor, at least one sample of at least one calibration mixture, which contains components in known concentrations, is analyzed in the gas-chromatograph based on the calibration and relative response factors being determined based on the obtained detector responses and the known concentrations and being stored in the evaluation device, the method comprising:

comparing, based on the calibration, the determined relative response factors in the evaluation device with universal relative response factors typical of the detector device; and generating and outputting an error message by the evaluation device, if the relative response factors determined during the calibration deviate beyond a predetermined degree from the universal relative response factors;

wherein the universal relative response factors are unchangeable.

2. The method as claimed in claim 1, wherein the universal relative response factors are determined and provided by the manufacturer of at least one of (i) the detector device and (ii) the gas chromatograph.

3. The method as claimed in claim 1, wherein the universal relative response factors are provided in electronic form.

4. The method as claimed in claim 2, wherein the universal relative response factors are provided in electronic form.

5. The method as claimed in claim 3, wherein the universal relative response factors are provided on a remote computer which is accessible via the Internet and retrievable from the Internet.

6. The method as claimed in claim 1, wherein the universal relative response factors of the detector device are given as a device description.

7. The method as claimed in claim 2, wherein the universal relative response factors of the detector device are given as a device description.

8. The method as claimed in claim 3, wherein the universal relative response factors of the detector device are given as a device description.

9. The method as claimed in claim 1, wherein the evaluation device identifies a deviation pattern and based on this reports an error cause in an event deviations extending beyond a predetermined degree are established with a number of components.

10. A gas chromatograph comprising:
a dosing device, a separating device, a detector device and an evaluation device with a calibration data memory, which are arranged and configured to dose a sample of a mixture of materials to be analyzed, route the dosed sample in order to separate components contained in the mixture of materials via the separating device, detect selected separated components at an end thereof and to quantitatively determine their concentrations in the mixture of materials based on detector responses supplied by the detector device and response factors stored in the evaluation device;
wherein a determination of the concentration of at least one first component of the mixture of materials is performed as a function of the detector response to the at least one first component, the determined or known concentration of a second component of the mixture of materials and a relative response factor;
wherein the evaluation device is further configured to determine relative response factors while calibrating the gas chromatograph with at least one sample of at least one calibration mixture contained in the known concentrations based on the detector responses obtained and the known concentrations and to store the relative response factors in the calibration data memory;
wherein the evaluation device includes a memory and a comparison device, which is configured to compare the relative response factors determined during the calibration with universal relative response factors representative of the detector device and contained in the memory and to generate an error message and to output the error message if the relative response factors determined during the calibration deviate beyond a predetermined degree from the universal relative response factors; and
wherein the universal relative response factors are unchangeable.

11. The gas chromatograph as claimed in claim 10, wherein the evaluation device includes at least one data interface for receiving the universal relative response factors.

12. The gas chromatograph as claimed in claim 11, wherein the data interface is configured to receive the universal relative response factors from a remote computer which is accessible via the Internet.

13. The gas chromatograph as claimed in claim 11, wherein the data interface is configured to read out the universal relative response factors from a data carrier in a wired or wireless manner.

14. The gas chromatograph as claimed in claim 12, wherein the data interface is configured to read out the universal relative response factors from a data carrier in a wired or wireless manner.

15. The gas chromatograph as claimed in claim 14, wherein the data carrier consists of a data carrier arranged on the detector device.

16. The gas chromatograph as claimed in claim 15, wherein the data carrier comprises a storage chip.

17. The gas chromatograph as claimed in claim 10, wherein the evaluation device is further configured to identify a deviation pattern and provide a notification of an error cause based on the deviation pattern in an event that deviations extending beyond the predetermined degree are established with a number of components.

* * * * *